US010102653B2

(12) United States Patent
Rickes et al.

(10) Patent No.: US 10,102,653 B2
(45) Date of Patent: Oct. 16, 2018

(54) METHODS AND SYSTEMS FOR IDENTIFYING POLYMERASE CHAIN REACTION SITES

(71) Applicant: LIFE TECHNOLOGIES CORPORATION, Carlsbad, CA (US)

(72) Inventors: Scott Rickes, San Diego, CA (US); Lik Seng Lau, Singapore (SG); Kok Siong Teo, Singapore (SG); Zeng Wei Chu, Singapore (SG); Lian Seng Loh, Singapore (SG); Vanee Pho, San Francisco, CA (US); Michael Uy, Singapore (SG); David Hoard, Escondido, CA (US); Sean Zimmerman, San Diego, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 15/017,136

(22) Filed: Feb. 5, 2016

(65) Prior Publication Data

US 2016/0239990 A1 Aug. 18, 2016

Related U.S. Application Data

(60) Provisional application No. 62/113,006, filed on Feb. 6, 2015.

(51) Int. Cl.
*G06T 11/20* (2006.01)
*G01N 21/64* (2006.01)
(Continued)

(52) U.S. Cl.
CPC ........ *G06T 11/206* (2013.01); *G01N 21/6428* (2013.01); *G01N 21/6452* (2013.01);
(Continued)

(58) Field of Classification Search
None
See application file for complete search history.

(56) References Cited

U.S. PATENT DOCUMENTS

2011/0025717 A1* 2/2011 Gilmore .............. G06F 3/04855 345/661
2012/0231458 A1 9/2012 Bae

FOREIGN PATENT DOCUMENTS

WO 2003029924 A2 4/2003
WO WO2013049443 A1 * 9/2012
WO 2013049443 A1 4/2013

OTHER PUBLICATIONS

International Search Report and Written Opinion issued for International Patent Application No. PCT/US2016/016827 dated Jun. 14, 2016.

(Continued)

*Primary Examiner* — Vu Nguyen
(74) *Attorney, Agent, or Firm* — Mauriel Kapouytian Woods LLP; Andrew A. Noble; Michael Mauriel

(57) ABSTRACT

A method for identifying a reaction site associated with an amplification curve from a plurality of amplification curves is provided. Amplification data is received from a plurality of reaction sites, wherein each reaction site contains a sample. A plurality of amplification curves is generated from the amplification data and a first portion of the plurality of amplification curves is displayed on a display screen. A list of indications of reaction sites associated with the first portion of amplification curves is displayed alongside the first portion of amplification curves on the display screen. Then the view is adjusted to display a second portion of the plurality of amplification curves, and the list is dynamically adjusted to display indications of reaction sites associated with the second portion of amplification curves alongside (Continued)

100
102
104
106
108 the second portion of amplification curves on the display screen, wherein the list is configured to be scrollable.

20 Claims, 15 Drawing Sheets

(51) Int. Cl.

| | |
|---|---|
| ***G06F 19/26*** | (2011.01) |
| ***G06F 3/0482*** | (2013.01) |
| ***G06F 3/0484*** | (2013.01) |
| ***G06F 3/0485*** | (2013.01) |
| ***G06F 3/0488*** | (2013.01) |
| ***G06T 3/40*** | (2006.01) |

(52) U.S. Cl.
CPC .......... *G06F 3/0482* (2013.01); *G06F 3/0485* (2013.01); *G06F 3/0488* (2013.01); *G06F 3/04842* (2013.01); *G06F 19/26* (2013.01); *G06T 3/40* (2013.01); *G01N 21/6456* (2013.01)

(56) References Cited

OTHER PUBLICATIONS

Applied Biosystems, Applied Biosystems 7500 Fast and 7500 Real-Time PCR Systems, Specification Sheet, 2009, pp. 1-4, Life Technologies Corporation.
Applied Biosystems, Data Analysis on the ABI PRISM 7700 Sequence Detection System: Setting Baseline and Thresholds, 2002, pp. 1-12.

* cited by examiner

FIG. 5

METHODS AND SYSTEMS FOR IDENTIFYING POLYMERASE CHAIN REACTION SITES

CROSS-REFERENCE TO RELATED APPLICATIONS

This application claims the benefit of priority of U.S. Provisional Patent Application No. 62/113,006, filed on Feb. 6, 2015, which is incorporated herein in its entirety by reference.

BACKGROUND

Generally, users perform biological studies by gathering and comparing various sets of biological data. For example, a user may run various qPCR-based experiments to gather distinct types of biological data, such as genotyping data or gene expression data, about a gene of interest to the study. If the user wishes to compare various types of biological data, it is often done manually. The number of samples needed for one experiment may also be great and it is often difficult to isolate a particular sample for a user to examine and visualize so that a user may quickly and easily get valuable information from the data. Further, labs or facilities often operate several biological instruments. It may be difficult to track maintenance or calibration of the instruments

SUMMARY

In one exemplary embodiment, a method for identifying a reaction site associated with an amplification curve from a plurality of amplification curves is provided. The method includes receiving amplification data from a plurality of reaction sites, wherein each reaction site contains a sample and generating a plurality of amplification curves from the amplification data. The method further includes displaying a first portion of the plurality of amplification curves on a display screen, and displaying a list of indications of reaction sites associated with the first portion of amplification curves alongside the first portion of amplification curves on the display screen. The method includes adjusting the view to display a second portion of the plurality of amplification curves, and dynamically adjusting the list to display indications of reaction sites associated with the second portion of amplification curves alongside the second portion of amplification curves on the display screen. The list is configured to be scrollable.

In another exemplary embodiment, a computer-readable storage medium encoded with processor-executable instructions, the instruction for identifying a reaction site associated with an amplification curve from a plurality of amplification curves, is provided. The instructions comprising instructions for receiving amplification data from a plurality of reaction sites, wherein each reaction site contains a sample, and generating a plurality of amplification curves from the amplification data. The instructions further include instructions for displaying a first portion of the plurality of amplification curves on a display screen and displaying a list of indications of reaction sites associated with the first portion of amplification curves alongside the first portion of amplification curves on the display screen. The instructions further include instructions for adjusting the view to display a second portion of the plurality of amplification curves, and dynamically adjusting the list to display indications of reaction sites associated with the second portion of amplification curves alongside the second portion of amplification curves on the display screen. The list is configured to be scrollable.

In yet another exemplary embodiment, a system for identifying a reaction site associated with an amplification curve from a plurality of amplification curves is provided. The system includes a processor; and a memory. The memory is encoded instructions, executable by the processor. The instructions include instructions for receiving amplification data from a plurality of reaction sites, wherein each reaction site contains a sample, and generating a plurality of amplification curves from the amplification data. The instructions further include instructions for displaying a first portion of the plurality of amplification curves on a display screen and displaying a list of indications of reaction sites associated with the first portion of amplification curves alongside the first portion of amplification curves on the display screen. The instructions further include instructions for adjusting the view to display a second portion of the plurality of amplification curves, and dynamically adjusting the list to display indications of reaction sites associated with the second portion of amplification curves alongside the second portion of amplification curves on the display screen. The list is configured to be scrollable.

DESCRIPTION OF THE FIGURES

FIG. 5 illustrates an example of a graphical user interface for inputting tags or comments according to various embodiments described herein;

DETAILED DESCRIPTION

To provide a more thorough understanding of the present invention, the following description sets forth numerous specific details, such as specific configurations, parameters, examples, and the like. It should be recognized, however, that such description is not intended as a limitation on the scope of the present invention, but is intended to provide a better description of the exemplary embodiments.

Researchers use biological instrument to perform various experiments to study genes of interest. The present teachings are described with reference to Real-Time Polymerase Chain Reaction (RT-PCR) instruments. In particular, an embodiment of the present teachings is implemented for RT-PCR instruments employing optical imaging of well plates. Such instruments can be capable of simultaneously measuring signals from a plurality of samples, spots, or reaction sites for analytical purposes.

The measured signals include fluorescence data acquired from the plurality of reaction sites to detect the amount of nucleic acid within the reaction site over time as the sample within the reaction site is amplified. The fluorescence data for each reaction site is plotted to generate an amplification curve. Since fluorescence data is measure from every reaction site, there are often hundreds, sometimes thousands, of generated amplification curves. As one could imagine, to view a single amplification curve and associated information related to the sample, is challenging. According to various embodiments described herein, methods and systems allow a user to easily select a particular amplification curve that is of interest and view information associated with the amplification curve so that the user is able to quickly get useful information from the real-time amplification curves or mark the curves for further analysis later.

Figure 1:
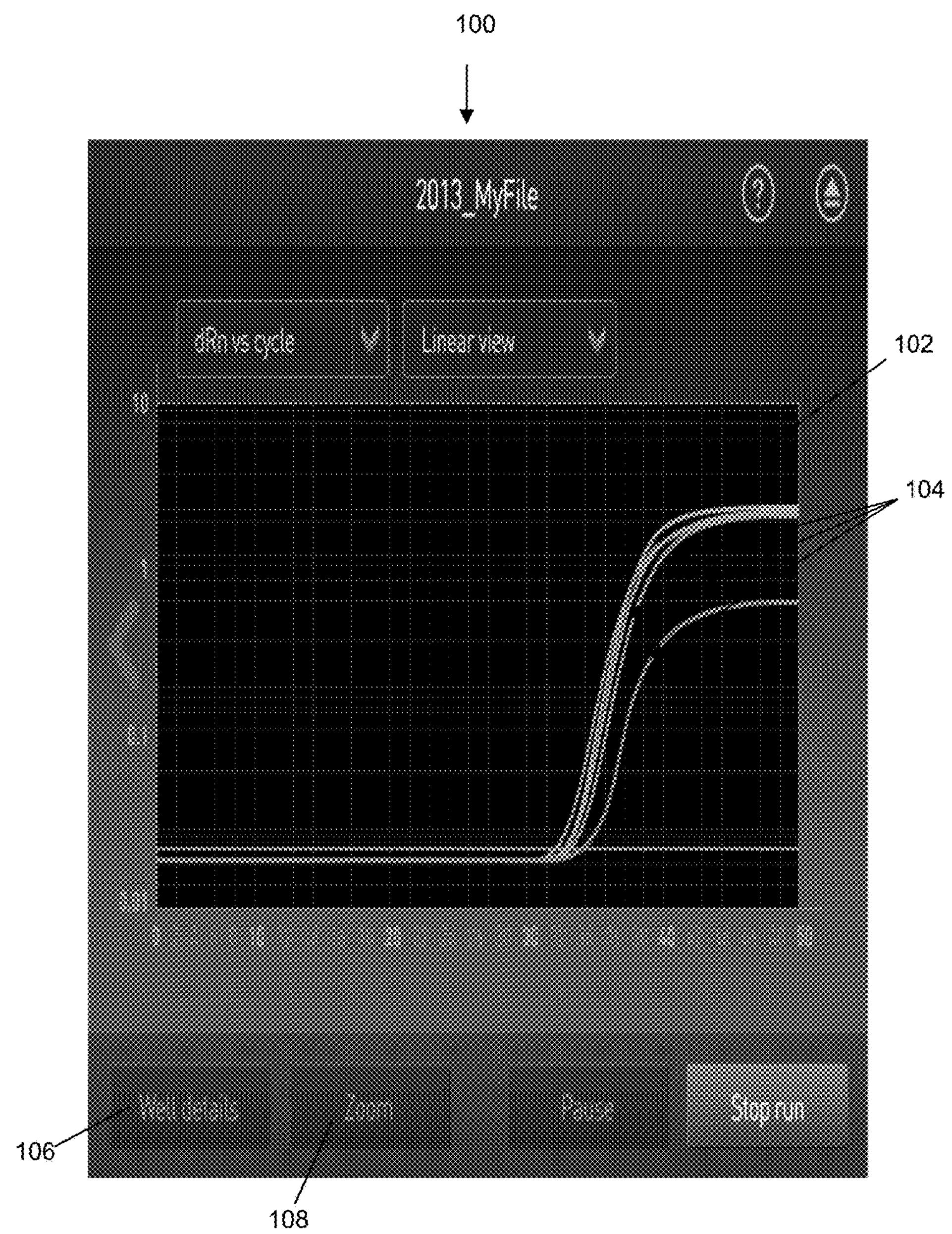
FIG. 1 illustrates an example of a graphical user interface for displaying amplification curves according to various embodiments described herein.

With reference to FIG. 1, a graphical user interface 100 displaying a plurality of amplification curves 104 within amplification curve plot 102 is depicted. For the portion of the plurality of amplification curves 104 visible in amplification curve plot 102, the details of each well associated with the amplification curve can be viewed by activating well detail button 106. Further, different portions of the plurality of amplification curves may be viewed by zooming or unzooming the amplification curve plot 102 by activating zoom button 108.

Figure 2:
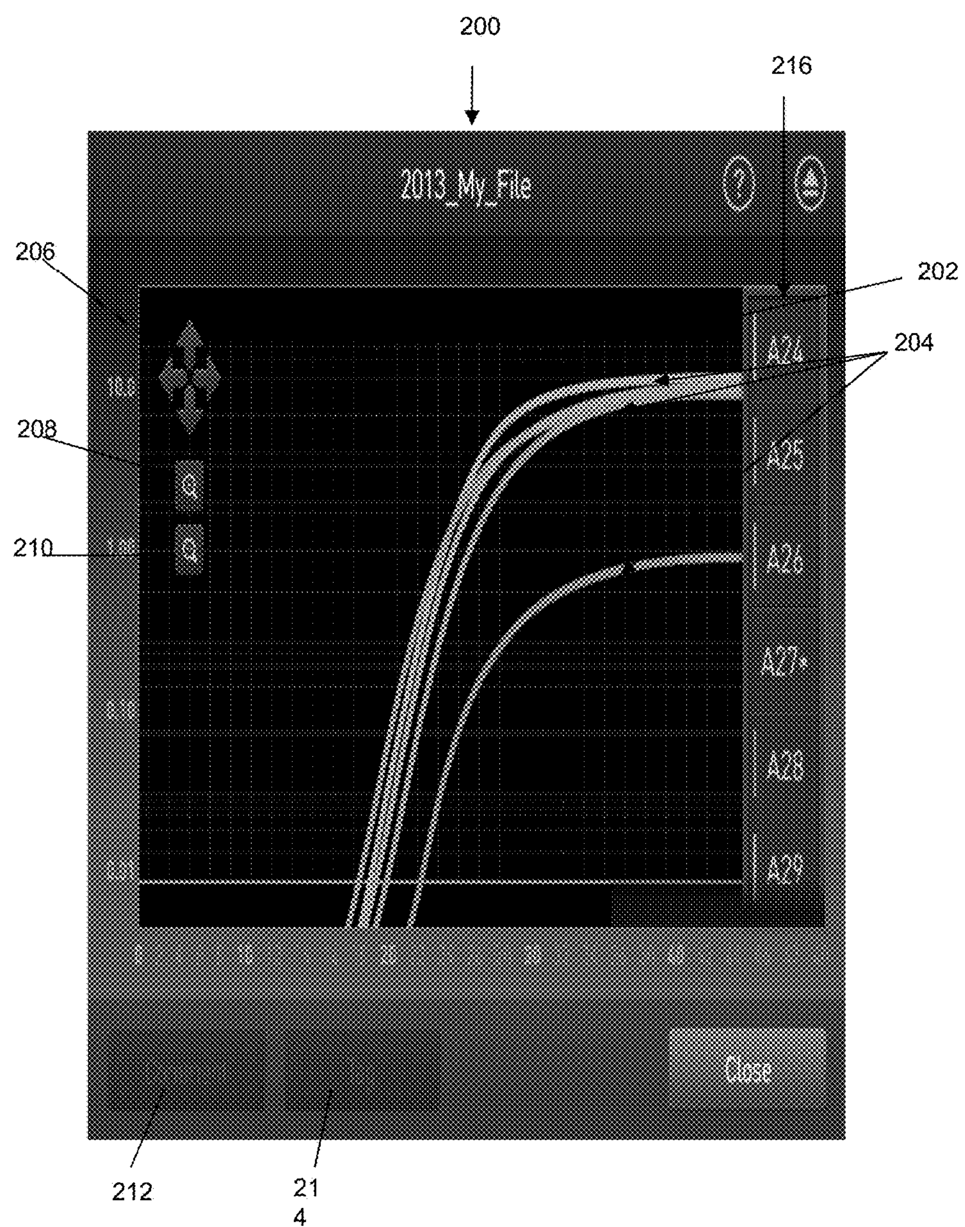
FIG. 2 illustrates an example of a graphical user interface for viewing a selection of amplification curves according to various embodiments described herein.

In another embodiment shown in FIG. 2, an example of a graphical user interface 200 for viewing a selection of amplification curves 204 is illustrated. In this example, amplification curve plot 202 displays a portion of amplification curves 204. The view of amplification curve plot 202 may be shifted by activating arrows 206. Further, the view of amplification curve plot 202 may be zoomed in by activating zoom button 308 or zoomed out using unzoom button 210. By changing the view of amplification curve plot 202, the portion of amplification curves displayed may dynamically change. In well scroll bar 216, further information for the viewable amplification curves are displayed. For example, well locations of amplification curves 204 are indicated by color in well scroll bar 216. If the number of amplification curves visible in amplification curve plot 202 exceeds the amount of available space in well scroll bar 216, the user may scroll down or up to view the information about the other amplification curve s. If more information is desired about a particular amplification curve, a user may select the associated well location information in well scroll bar 216 to view further details, such as sample type loaded into the well. In this way, individual amplification curves may be more easily selected and information associated with the selected amplification curve can be quickly and easily identified.

Additionally, according to various embodiments, a comment button 212 and tag button 214 may be provided to a user for the user to choose to add in a comment or a tag for a specific amplification curve. For example, a user may notice an amplification curve has an unusual characteristic and would like to make a comment associated with the amplification curve to store for future reference. Comment button 212 and tag button 214 may be selected by the user to input tags and/or comments.

Arrows 206, zoom in button 208, zoom out button 210, and well scroll bar 216 may be activated by touch control. In various embodiments, a user may also be able to perform pinch-to-zoom touch screen gestures on amplification curve plot 202 to zoom in and zoom out the viewable area of amplification curve plot 202. Well scroll bar 216 may also be controlled by touch screen gestures, such as flicking upwards to move well scroll bar 216 up or flicking downwards to move well scroll bar 216 down.

Figure 3:
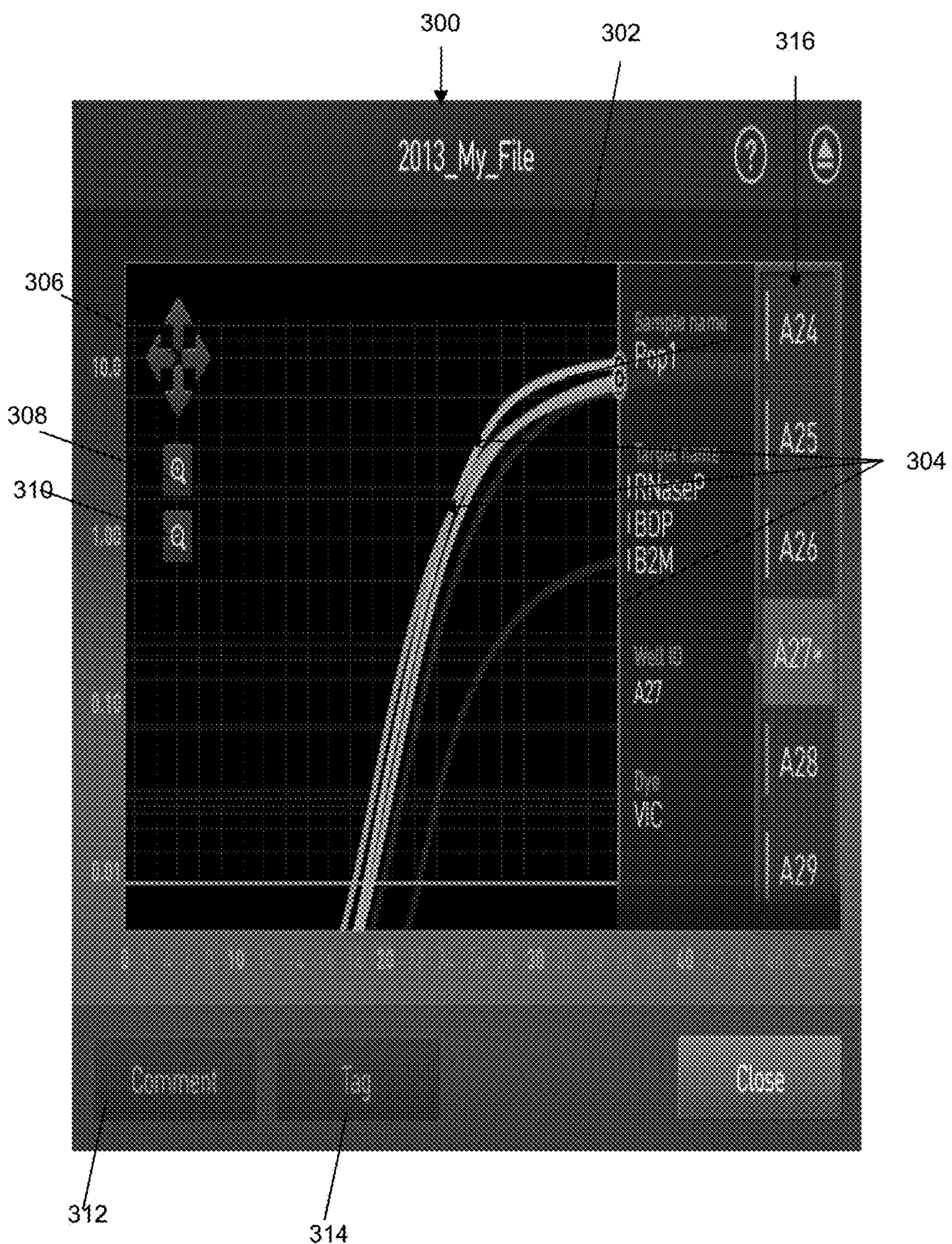
FIG. 3 illustrates an example of a graphical user interface for identifying amplification curves according to various embodiments described herein.

FIG. 3 illustrates another example of a graphical user interface 300 for identifying amplification curves according to various embodiments described herein. In this example, amplification curve plot 302 displays a portion of amplification curves 304. The view of amplification curve plot 302 may be shifted by activating arrows 306. Further, the view of amplification curve plot 302 may be zoomed in by activating zoom button 308 or zoomed out using zoom out button 310. By changing the view of amplification curve plot 302, the portion of amplification curves displayed may dynamically change. In well scroll bar 316, further information for the viewable amplification curves are displayed. For example, well locations of amplification curves 304 are indicated by color in well scroll bar 316. If the number of amplification curves visible in amplification curve plot 302 exceeds the amount of available space in well scroll bar 316, the user may scroll down or up to view the information about the other amplification curve s. If more information is desired about a particular amplification curve, a user may select the associated well location information in well scroll bar 316 to view further details, such as sample type loaded into the well. In this example, A27 is selected from well scroll bar 316. Other information associated with A27 is displayed adjacent to well scroll bar 316. Furthermore, the amplification curve associated with A27 may be highlighted in amplification curve plot 302 so that the user is able to easily identify all associated information to well A27. In this way, individual amplification curves may be more easily selected and information associated with the selected amplification curve can be quickly and easily identified.

Additionally, according to various embodiments, a comment button 312 and tag button 314 may be provided to a user for the user to choose to add in a comment or a tag for a specific amplification curve. For example, a user may notice an amplification curve has an unusual characteristic and would like to make a comment associated with the amplification curve to store for future reference. Comment button 312 and tag button 314 may be selected by the user to input tags and/or comments.

Arrows 306, zoom button 308, zoom out button 310, and well scroll bar 316 may be activated by touch control. In various embodiments, a user may also be able to perform pinch-to-zoom touch screen gestures on amplification curve plot 302 to zoom and zoom out the viewable area of amplification curve plot 302. Well scroll bar 316 may also be controlled by touch screen gestures, such as flicking upwards to move well scroll bar 316 up or flicking downwards to move well scroll bar 316 down.

Figure 4:
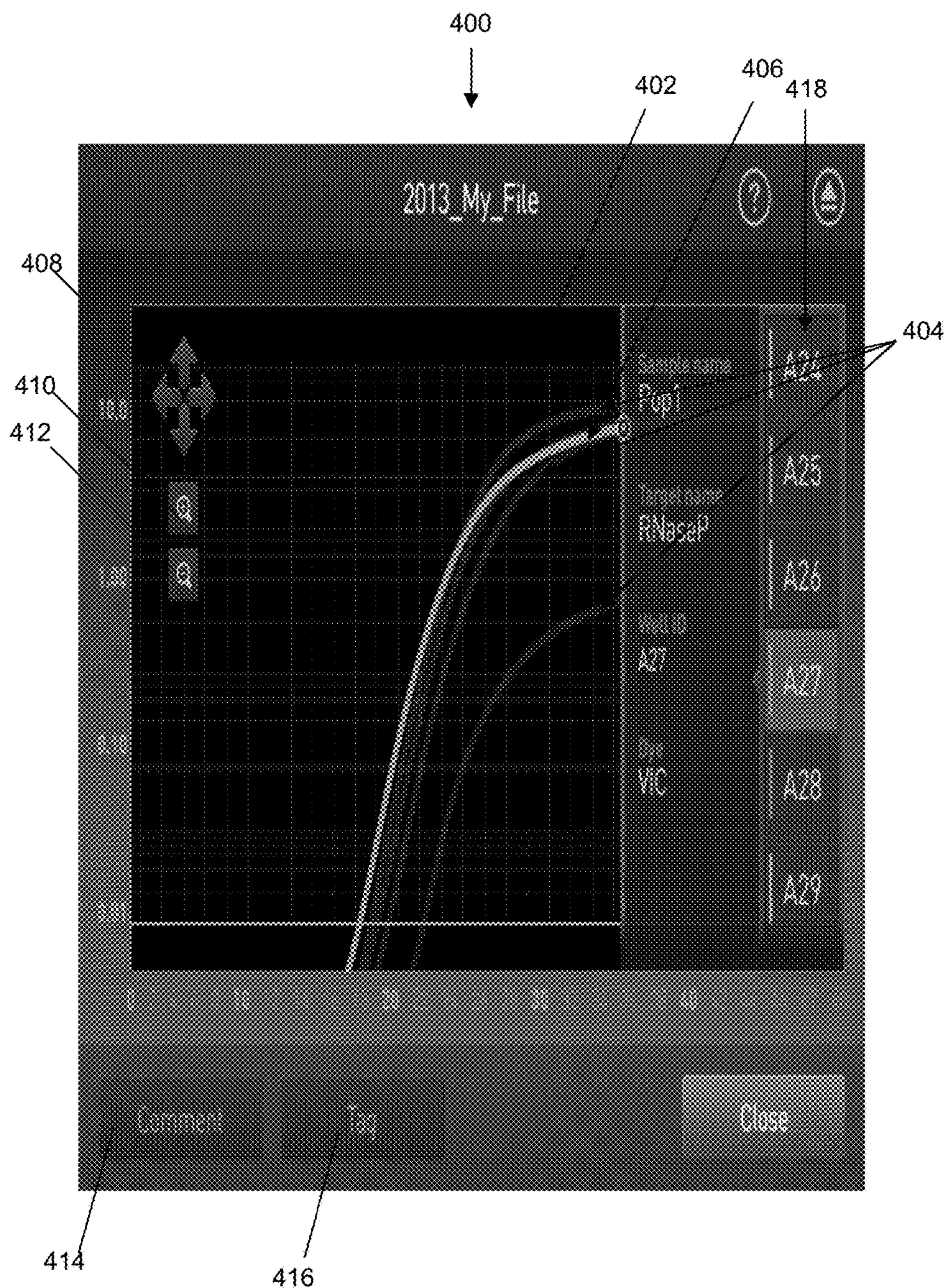
FIG. 4 illustrates an example of a graphical user interface for identifying amplification curves according to various embodiments of described herein.

FIG. 4 illustrates another example of a graphical user interface 400 for identifying amplification curves according to various embodiments of described herein. In this example, a selected amplification curve is shown highlighted in amplification plot 402. Well scroll bar 418 displays well location of the portion of a plurality of amplification curves 404. A user can select a particular well, in this case, A27 and view sample name, target name, well ID, and dye associated with A27. The amplification curve associated with A27 is shown to be in green. In addition to the color to identify the associated amplification curve, the system also displays the amplification curve associated with A27 406 in a highlighted manner so that the other curves are dimmed to highlight amplification curve 406.

FIG. 5 illustrates an example of a graphical user interface 500 for inputting tags or comments according to various embodiments described herein. With reference back to FIG. 4, comment button 414 and tag button 416 allow a user to choose to input a comment or tag for a selected amplification curve. Once a user selects comment button 414 or tag button 416, a keyboard is displayed to the user. The user may enter a comment or tag in the input field box 502 using the keyboard. The keyboard may also be displayed on a touch screen so that the user may directly interact with the images displayed.

Figure 6:
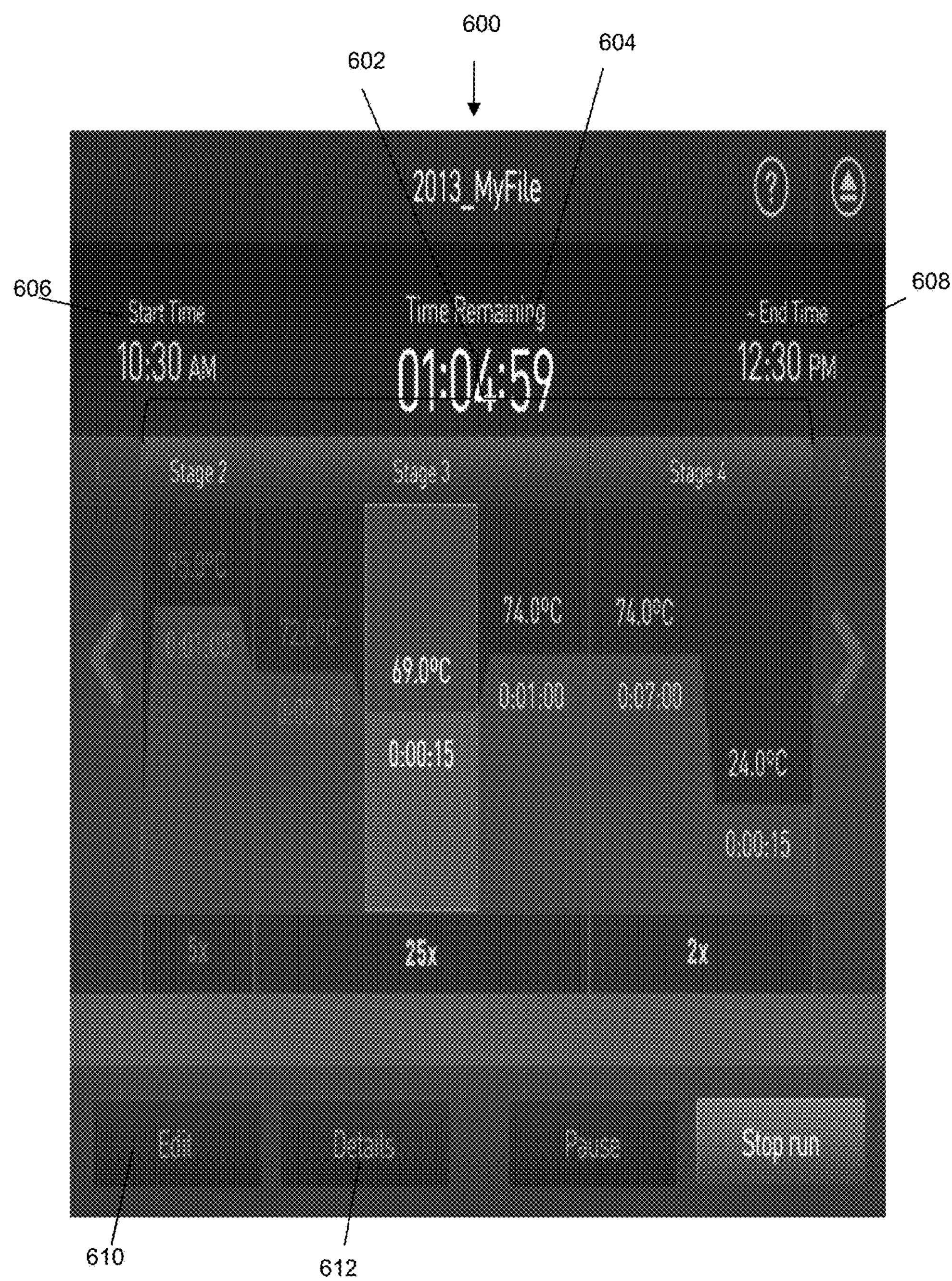
FIG. 6 illustrates an example of a graphical user interface for displaying and editing a thermal cycling protocol according to various embodiments described herein.

FIG. 6 illustrates an example of a graphical user interface for displaying and editing a thermal cycling protocol according to various embodiments described herein. A user may set up the thermal cycling protocol using graphical user interface 600. The user may adjust the protocol before the run is started on the instrument. The user may also adjust the protocol after the run has started. If the user wants to revise/adjust the thermal cycling protocol, the user may select the portion of the graphical representation of the thermal cycling protocol 602 they wish to edit and then select the edit button 610. The user may then adjust the temperature or length of a particular portion of the cycle, for example. This feature allows a user to make on the fly changes without having to stop the entire experiment run.

Additionally, the user is able to view the start time 606, end time 608 and time remaining for the experiment 604. GUI 600 may also be displayed on a touch screen capable of being activated by a user interacting directly with GUI 600.

Figure 7:
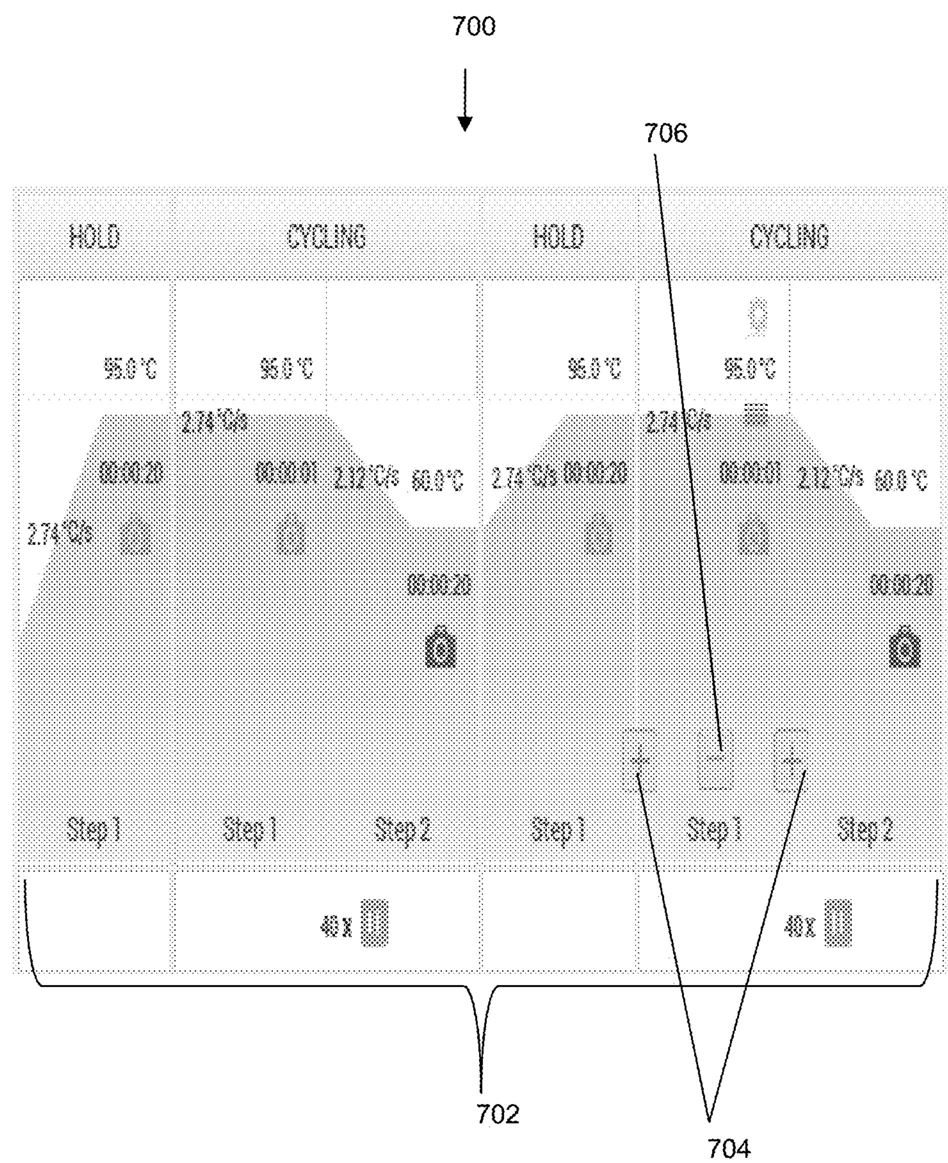
FIG. 7 illustrates an example of a graphical user interface for displaying and editing a thermal cycling protocol according to various embodiments described herein.

FIG. 7 illustrates another example of a graphical user interface for displaying and editing a thermal cycling protocol according to various embodiments described herein. In this example, the user can add or delete from the graphical representation of the thermal cycling protocol 702 by activating the addition buttons 704 or deletion button 706.

Figure 8:
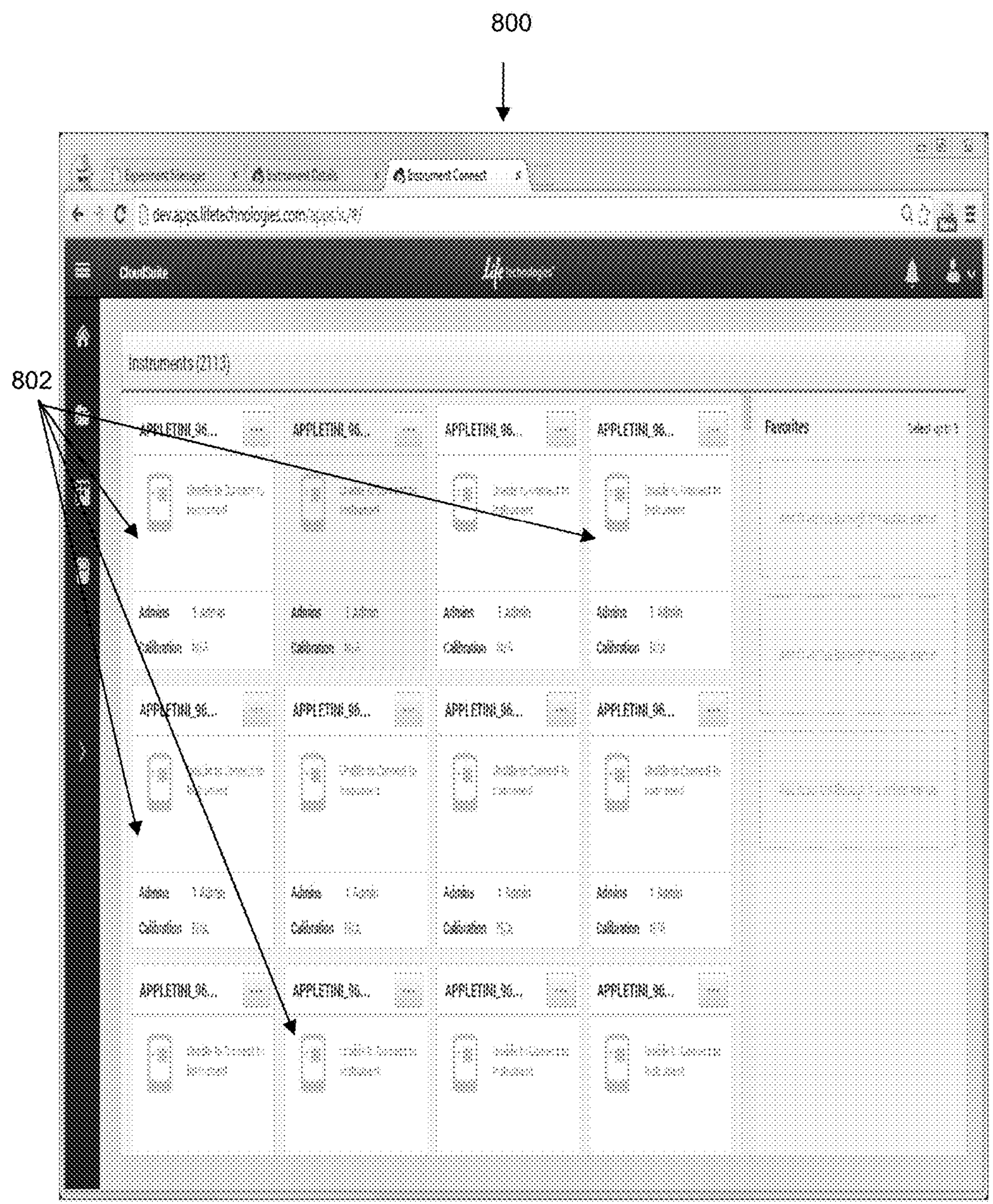
FIG. 8 illustrates an example of a graphical user interface for displaying a plurality of instrument status according to various embodiments described herein.

In a laboratory setting, there is often multiple instruments used by the researchers using the lab. It is often difficult to monitor that status, and routine maintenance and calibration schedules of the instruments. According to various embodiments described herein, GUI 800 may be displayed to a user to indicate the status of each of the instruments in the network of instruments used by a lab, for example. With reference to FIG. 8, a graphical user interface 800 for displaying a plurality of instrument statuses 802 according to various embodiments described herein is depicted. A user viewing GUI 800 can view the instruments within the same network and easily view the instrument status, such as available or in use, and other information such as calibration status. More detailed information about an individual instrument may also be viewed.

Figure 9:
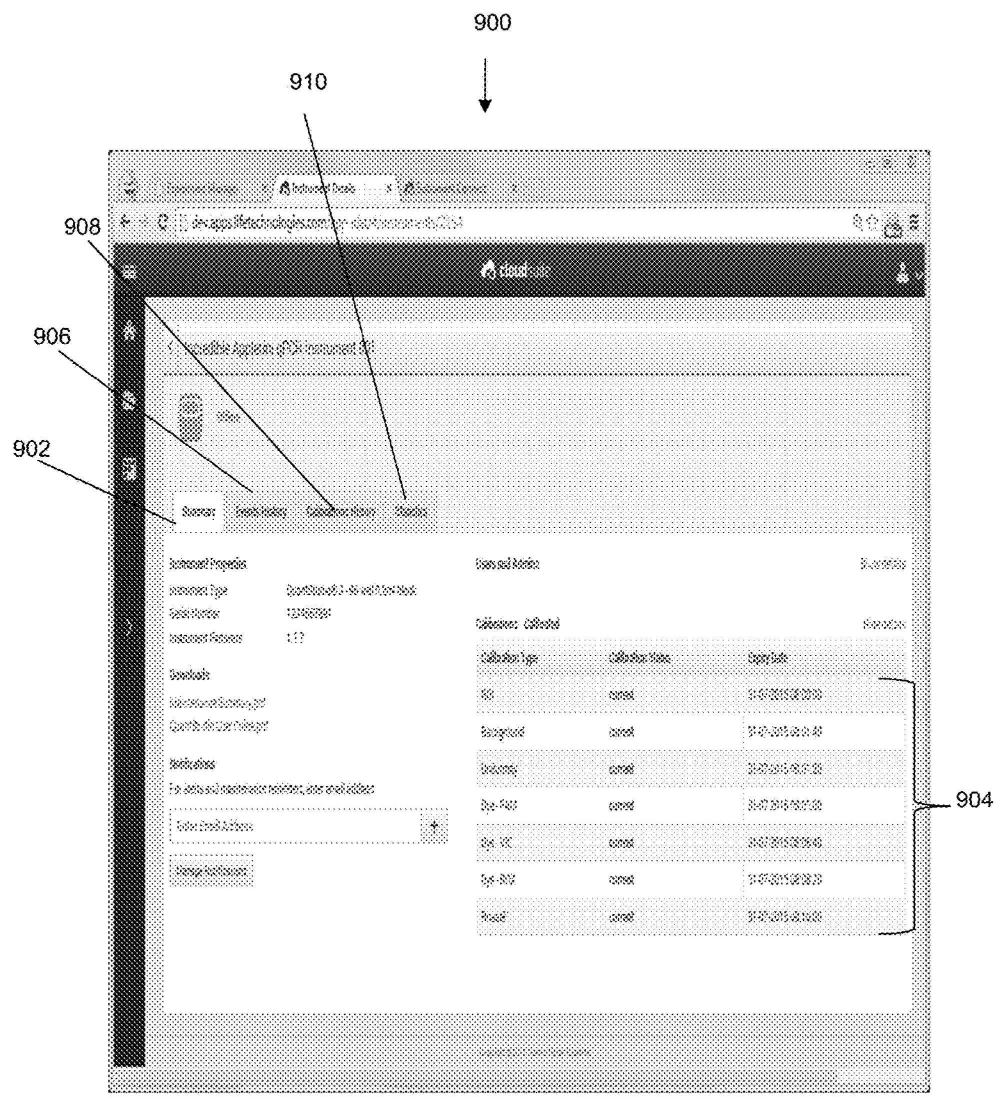
FIG. 9 illustrates an example of a graphical user interface for displaying information about an instrument according to various embodiments described herein.

FIG. 9 illustrates an example of a graphical user interface 900 for displaying information about an instrument according to various embodiments described herein. GUI 900 illustrates a summary page 902 for an individual instrument. The various calibration statuses and expiration dates are viewed in the calibration status table 904. A user may also choose to view event history tab 906, calibration history tab 908, and statistics tab 910. In summary page 902, a user is able to view the calibration status of the instrument.

Figure 10:
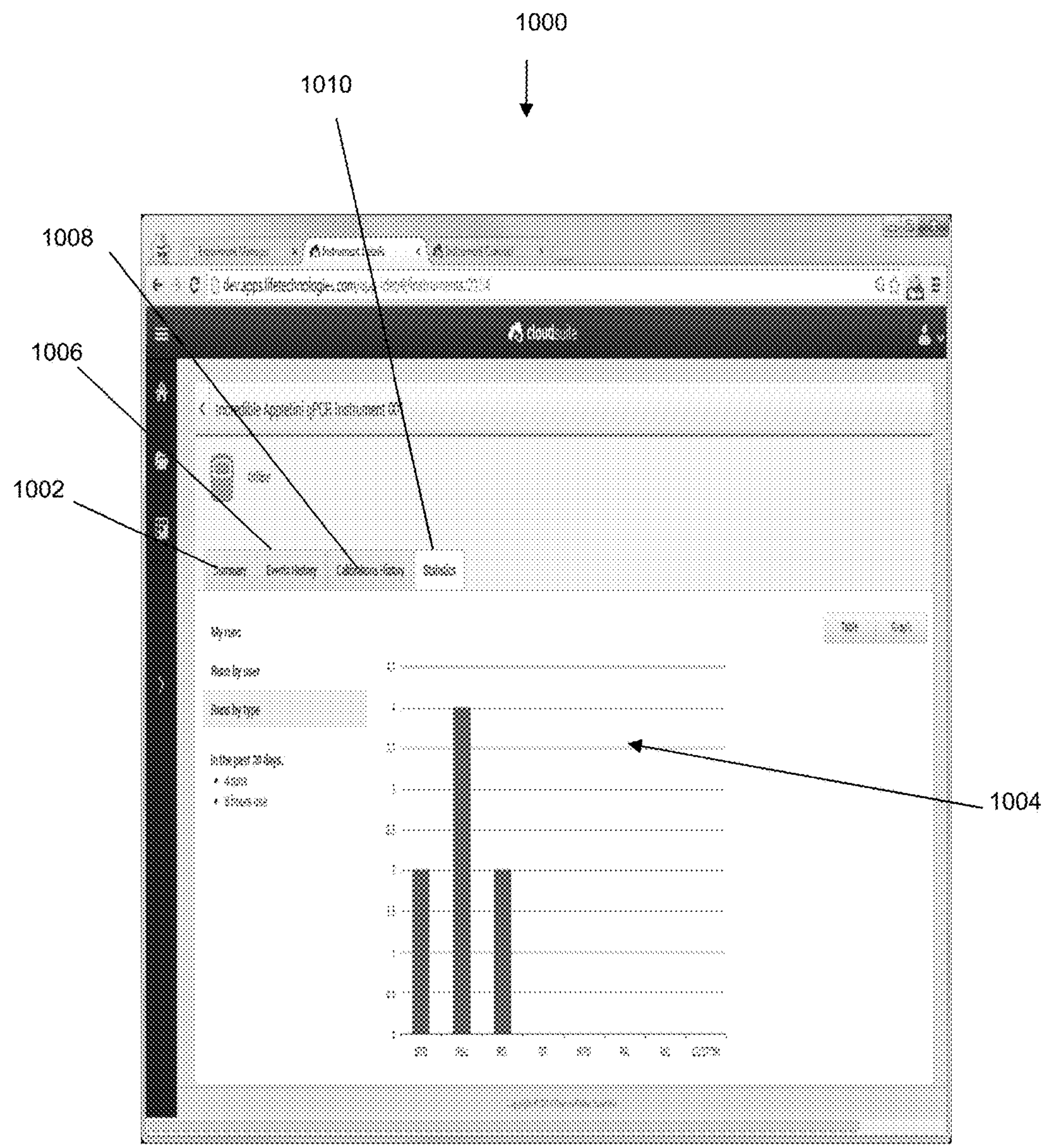
FIG. 10 illustrates an example of a graphical user interface for displaying statistical information about an instrument according to various embodiments described herein.

FIG. 10 illustrates an example of a graphical user interface 1000 for displaying statistical information about an instrument according to various embodiments described herein. The statistic page 1010 shows the type of runs this particular instrument for which this instrument has been used. Statistics page 1010 also indicates the number of hours of usage of this experiment.

Figure 11:
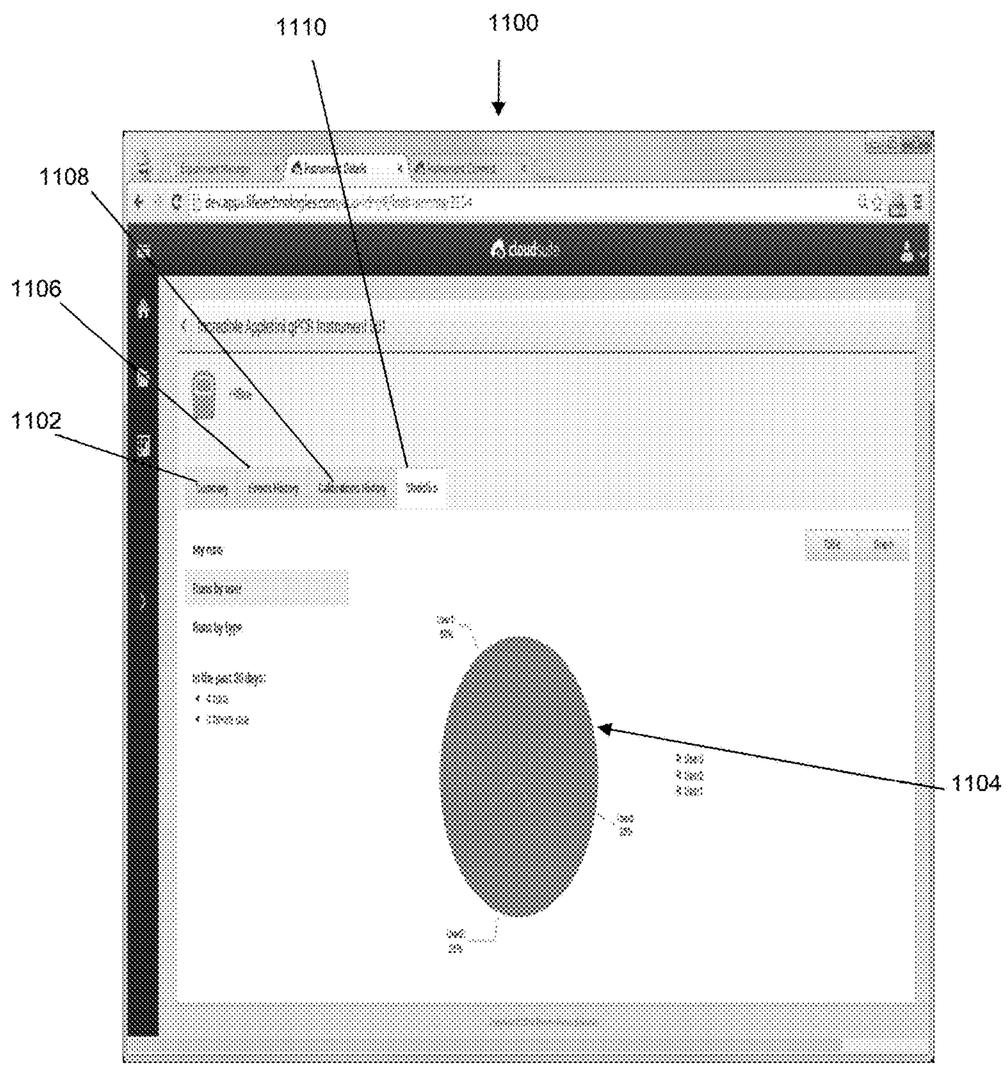
FIG. 11 illustrates an example of a graphical user interface for displaying statistical information about an instrument according to various embodiments described herein.

FIG. 11 illustrates another example of a graphical user interface 1100 for displaying statistical information about an instrument according to various embodiments described herein. In this example, pie chart 1104 graphically shows the amount of use of the instrument by user. Pie chart 1104 shows that this instrument has been used most often by user 1.

Computer-Implemented System

Those skilled in the art will recognize that the operations of the various embodiments may be implemented using hardware, software, firmware, or combinations thereof, as appropriate. For example, some processes can be carried out using processors or other digital circuitry under the control of software, firmware, or hard-wired logic. (The term "logic" herein refers to fixed hardware, programmable logic and/or an appropriate combination thereof, as would be recognized by one skilled in the art to carry out the recited functions.) Software and firmware can be stored on non-transitory computer-readable media. Some other processes can be implemented using analog circuitry, as is well known to one of ordinary skill in the art. Additionally, memory or other storage, as well as communication components, may be employed in embodiments of the invention.

Figure 12:
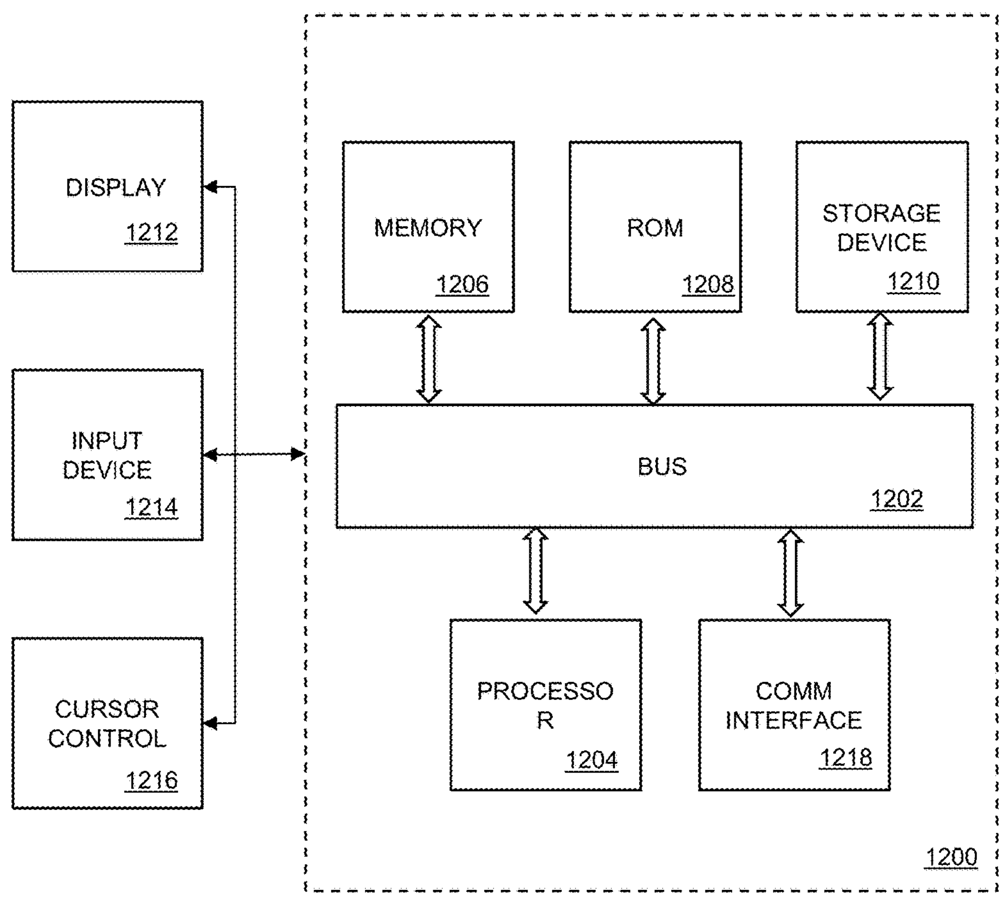
FIG. 12 illustrates a computing system upon which various embodiments described herein may be implemented.

FIG. 12 is a block diagram that illustrates a computer system 1200 that may be employed to carry out processing functionality, according to various embodiments. Instruments to perform experiments may be connected to the exemplary computing system 1200. Computing system 1200 can include one or more processors, such as a processor 1204. Processor 1204 can be implemented using a general or special purpose processing engine such as, for example, a microprocessor, controller or other control logic. In this example, processor 1204 is connected to a bus 1202 or other communication medium.

Further, it should be appreciated that a computing system 1200 of FIG. 12 may be embodied in any of a number of forms, such as a rack-mounted computer, mainframe, supercomputer, server, client, a desktop computer, a laptop computer, a tablet computer, hand-held computing device (e.g., PDA, cell phone, smart phone, palmtop, etc.), cluster grid, netbook, embedded systems, or any other type of special or general purpose computing device as may be desirable or appropriate for a given application or environment. Additionally, a computing system 1200 can include a conventional network system including a client/server environment and one or more database servers, or integration with LIS/LIMS infrastructure. A number of conventional network systems, including a local area network (LAN) or a wide area network (WAN), and including wireless and/or wired components, are known in the art. Additionally, client/server environments, database servers, and networks are well documented in the art. According to various embodiments described herein, computing system 1200 may be configured to connect to one or more servers in a distributed network. Computing system 1200 may receive information or updates from the distributed network. Computing system 1200 may also transmit information to be stored within the distributed network that may be accessed by other clients connected to the distributed network.

Computing system 1200 may include bus 1202 or other communication mechanism for communicating information, and processor 1204 coupled with bus 1202 for processing information.

Computing system 1200 also includes a memory 1206, which can be a random access memory (RAM) or other dynamic memory, coupled to bus 1202 for storing instructions to be executed by processor 1204. Memory 1206 also may be used for storing temporary variables or other intermediate information during execution of instructions to be executed by processor 1204. Computing system 1200 further includes a read only memory (ROM) 1208 or other static storage device coupled to bus 1202 for storing static information and instructions for processor 1204.

Computing system 1200 may also include a storage device 1210, such as a magnetic disk, optical disk, or solid state drive (SSD) is provided and coupled to bus 1202 for storing information and instructions. Storage device 1210 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. As these examples illustrate, the storage media may include a computer-readable storage medium having stored therein particular computer software, instructions, or data.

In alternative embodiments, storage device 1210 may include other similar instrumentalities for allowing computer programs or other instructions or data to be loaded into computing system 1200. Such instrumentalities may include, for example, a removable storage unit and an interface, such as a program cartridge and cartridge interface, a removable memory (for example, a flash memory or other removable memory module) and memory slot, and other removable storage units and interfaces that allow software and data to be transferred from the storage device 1210 to computing system 1200.

Computing system 1200 can also include a communications interface 1218. Communications interface 1218 can be used to allow software and data to be transferred between computing system 1200 and external devices. Examples of communications interface 1218 can include a modem, a network interface (such as an Ethernet or other NIC card), a communications port (such as for example, a USB port, a RS-232C serial port), a PCMCIA slot and card, Bluetooth, etc. Software and data transferred via communications interface 1218 are in the form of signals which can be electronic, electromagnetic, optical or other signals capable of being received by communications interface 1218. These signals may be transmitted and received by communications interface 1218 via a channel such as a wireless medium, wire or cable, fiber optics, or other communications medium. Some examples of a channel include a phone line, a cellular phone link, an RF link, a network interface, a local or wide area network, and other communications channels.

Computing system 1200 may be coupled via bus 1202 to a display 1212, such as a cathode ray tube (CRT) or liquid crystal display (LCD), for displaying information to a computer user. An input device 1214, including alphanumeric and other keys, is coupled to bus 1202 for communicating information and command selections to processor 1204, for example. An input device may also be a display, such as an LCD display, configured with touchscreen input capabilities. Another type of user input device is cursor control 1216, such as a mouse, a trackball or cursor direction keys for communicating direction information and command selections to processor 1204 and for controlling cursor movement on display 1212. This input device typically has two degrees of freedom in two axes, a first axis (e.g., x) and a second axis (e.g., y), that allows the device to specify positions in a plane. A computing system 1200 provides data processing and provides a level of confidence for such data. Consistent with certain implementations of embodiments of the present teachings, data processing and confidence values are provided by computing system 1200 in response to processor 1204 executing one or more sequences of one or more instructions contained in memory 1206. Such instructions may be read into memory 1206 from another computer-readable medium, such as storage device 1210. Execution of the sequences of instructions contained in memory 1206 causes processor 1204 to perform the process states described herein. Alternatively hard-wired circuitry may be used in place of or in combination with software instructions to implement embodiments of the present teachings. Thus implementations of embodiments of the present teachings are not limited to any specific combination of hardware circuitry and software.

The term "computer-readable medium" and "computer program product" as used herein generally refers to any media that is involved in providing one or more sequences or one or more instructions to processor 1204 for execution. Such instructions, generally referred to as "computer program code" (which may be grouped in the form of computer programs or other groupings), when executed, enable the computing system 1200 to perform features or functions of embodiments of the present invention. These and other forms of non-transitory computer-readable media may take many forms, including but not limited to, non-volatile media, volatile media, and transmission media. Non-volatile media includes, for example, solid state, optical or magnetic disks, such as storage device 1210. Volatile media includes dynamic memory, such as memory 1206. Transmission media includes coaxial cables, copper wire, and fiber optics, including the wires that comprise bus 1202.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 1204 for execution. For example, the instructions may initially be carried on magnetic disk of a remote computer. The remote computer can load the instructions into its dynamic memory and send the instructions over a telephone line using a modem. A modem local to computing system 1200 can receive the data on the telephone line and use an infra-red transmitter to convert the data to an infra-red signal. An infra-red detector coupled to bus 1202 can receive the data carried in the infra-red signal and place the data on bus 1202. Bus 1202 carries the data to memory 1206, from which processor 1204 retrieves and executes the instructions. The instructions received by memory 1206 may optionally be stored on storage device 1210 either before or after execution by processor 1204.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

Distributed System

Figure 13:
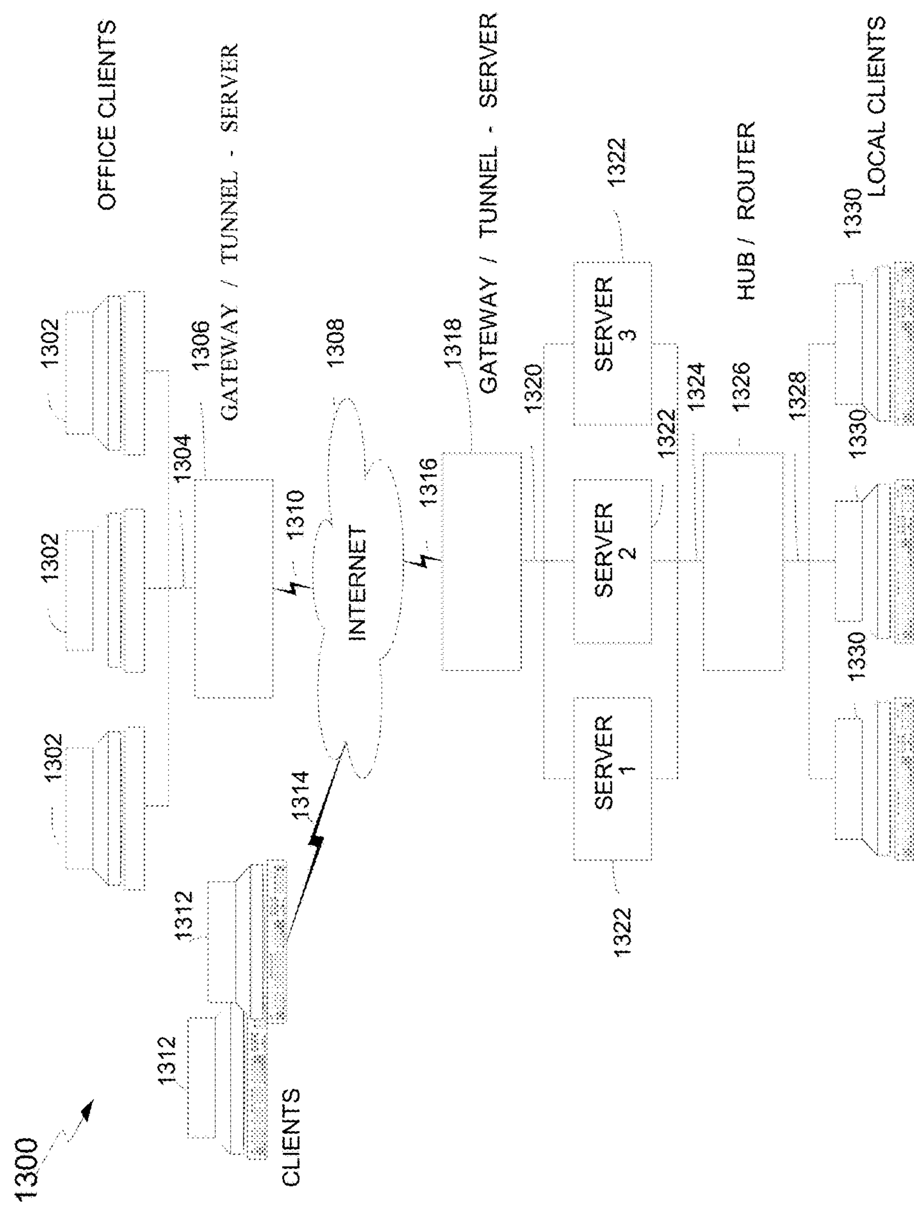
FIG. 13 illustrates an exemplary distributed network system according to various embodiments described herein.

Some of the elements of a typical Internet network configuration 1300 are shown in FIG. 13, wherein a number of client machines 1302 possibly in a remote local office, are shown connected to a gateway/hub/tunnel-server/etc 1310 which is itself connected to the internet 1308 via some internet service provider (ISP) connection 1310. Also shown are other possible clients 1312 similarly connected to the internet 1308 via an ISP connection 1314, with these units communicating to possibly a central lab or office, for example, via an ISP connection 1316 to a gateway/tunnel-server 1318 which is connected 1320 to various enterprise application servers 1322 which could be connected through another hub/router 1326 to various local clients 1330. Any of these servers 1322 could function as a development server for the analysis of potential content management and delivery design solutions as described in the present invention, as more fully described below.

PCR Instruments

Figure 14:
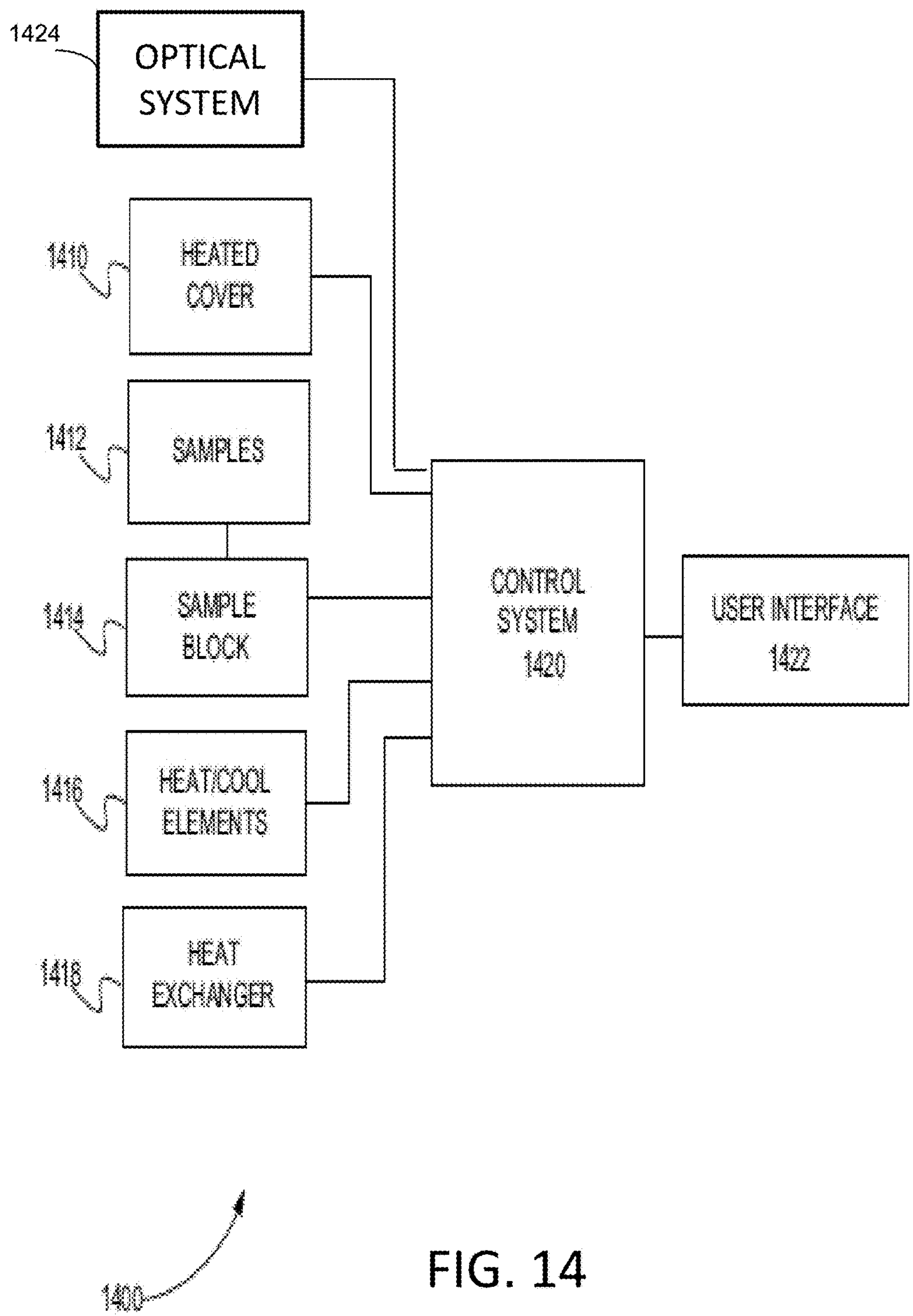
FIG. 14 is a block diagram that illustrates a PCR instrument 1400 upon which embodiments of the present teachings may be implemented.

As mentioned above, an instrument that may be utilized according to various embodiments, but is not limited to, is a polymerase chain reaction (PCR) instrument. FIG. 14 is a block diagram that illustrates a PCR instrument 1400, upon which embodiments of the present teachings may be implemented. PCR instrument 1400 may include a heated cover 1410 that is placed over a plurality of samples 1412 contained in a substrate (not shown). In various embodiments, a substrate may be a glass or plastic slide with a plurality of sample regions, which sample regions have a cover between the sample regions and heated cover 1410. Some examples of a substrate may include, but are not limited to, a multi-well plate, such as a standard microtiter 96-well, a 384-well plate, or a microcard, or a substantially planar support, such as a glass or plastic slide. The reaction sites in various embodiments of a substrate may include depressions, indentations, ridges, and combinations thereof, patterned in regular or irregular arrays formed on the surface of the substrate. Various embodiments of PCR instruments include a sample block 1414, elements for heating and cooling 1416, a heat exchanger 1418, control system 1420, and user interface 1422. Various embodiments of a thermal block assembly according to the present teachings comprise components 1414-1418 of PCR instrument 1400 of FIG. 14.

Real-time PCR instrument 1400 has an optical system 1424. In FIG. 14, an optical system 1424 may have an illumination source (not shown) that emits electromagnetic energy, an optical sensor, detector, or imager (not shown), for receiving electromagnetic energy from samples 1412 in a substrate, and optics 1440 used to guide the electromagnetic energy from each DNA sample to the imager. For embodiments of PCR instrument 1400 in FIG. 14 and real-time PCR instrument 1400 in FIG. 14, control system 1420, may be used to control the functions of the detection system, heated cover, and thermal block assembly. Control system 1420 may be accessible to an end user through user interface 1422 of PCR instrument 1400 in FIG. 14 and real-time PCR instrument 1400 in FIG. 14. Also a computer system 1400, as depicted in FIG. 14, may serve as to provide the control the function of PCR instrument 1400 in FIG. 14, as well as the user interface function. Additionally, computer system 400 of FIG. 4 may provide data processing, display and report preparation functions. All such instrument control functions may be dedicated locally to the PCR instrument, or computer system 400 of FIG. 4 may provide remote control of part or all of the control, analysis, and reporting functions, as will be discussed in more detail subsequently.

Optical System for Imaging

Figure 15:
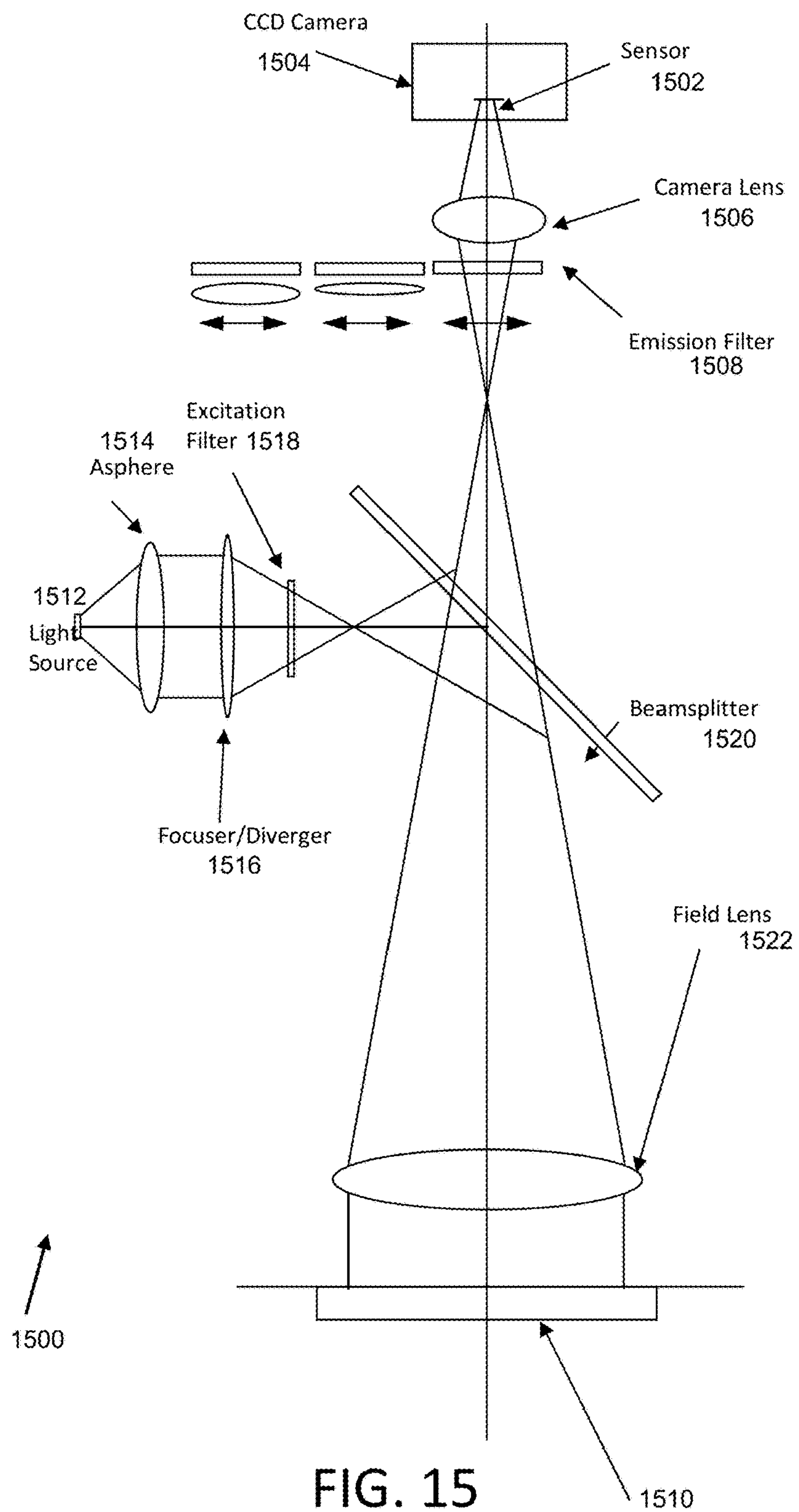
FIG. 15 depicts an exemplary optical system 1500 that may be used for imaging according to embodiments described herein.

FIG. 15 depicts an exemplary optical system 1500 that may be used for imaging according to embodiments described herein. It should be recognized that optical system 1500 is an exemplary optical system and one skilled in the art would recognize that other optical systems may be used to capture images an object-of-interest. According to various embodiments, an object of interest may be a sample holder such as, for example, a calibration plate as described herein. An optical sensor 1502 included in a camera 1504, for example, may image an object-of-interest 1510. The optical sensor 1502 may be a CCD sensor and the camera 1504 may be a CCD camera. Further, the optical sensor includes a camera lens 1506.

Depending on the object of interest, an emission filter 1508 can be chosen for imagining the object-of-interest 1510 according to various embodiments. Emission filter 1508 may be changed to image fluorescent emission emitted from the object-of-interest 1501 in other embodiments.

Optical system 1500 may use a reflected light source 1512 to image object-of-interest 1510. The light from light source 1512 may be filtered through an asphere 1514, a focuser/diverger 1516, and excitation filter 1518 before being reflected to the object-of-interest 1510 by beamsplitter 1520. Optical system 1500 may also include a field lens 1522. Depending on the object of interest, the excitation filter 1518 can be chosen or changed for imagining the object-of-interest 1510 according to various embodiments.

In example 1, a method for identifying a reaction site associated with an amplification curve from a plurality of amplification curves is provided. The method comprises: receiving amplification data from a plurality of reaction sites, wherein each reaction site contains a sample; generating a plurality of amplification curves from the amplification data; displaying a first portion of the plurality of amplification curves on a display screen; displaying a list of indications of reaction sites associated with the first portion of amplification curves alongside the first portion of amplification curves on the display screen; adjusting the view to display a second portion of the plurality of amplification curves; dynamically adjusting the list to display indications of reaction sites associated with the second portion of amplification curves alongside the second portion of amplification curves on the display screen, wherein the list is configured to be scrollable.

In example 2, a computer-readable storage medium encoded with processor-executable instructions, the instruction for identifying a reaction site associated with an amplification curve from a plurality of amplification curves. The instructions comprise instructions for: receiving amplification data from a plurality of reaction sites, wherein each reaction site contains a sample; generating a plurality of amplification curves from the amplification data; displaying a first portion of the plurality of amplification curves on a display screen; displaying a list of indications of reaction sites associated with the first portion of amplification curves alongside the first portion of amplification curves on the display screen; adjusting the view to display a second portion of the plurality of amplification curves; dynamically adjusting the list to display indications of reaction sites associated with the second portion of amplification curves alongside the second portion of amplification curves on the display screen, wherein the list is configured to be scrollable.

In example 3, a system for identifying a reaction site associated with an amplification curve from a plurality of amplification curves. The system comprises: a processor; and a memory encoded instructions, executable by the processor, the instructions comprising instructions for: receiving amplification data from a plurality of reaction sites, wherein each reaction site contains a sample; generating a plurality of amplification curves from the amplification data; displaying a first portion of the plurality of amplification curves on a display screen; displaying a list of indications of reaction sites associated with the first portion of amplification curves alongside the first portion of amplification curves on the display screen; adjusting the view to display a second portion of the plurality of amplification curves; dynamically adjusting the list to display indications of reaction sites associated with the second portion of amplification curves alongside the second portion of amplification curves on the display screen, wherein the list is configured to be scrollable.

In example 4, the examples 1, 2, 3, or any of the preceding examples are provided, wherein the adjusting the view is zooming in on the plurality of amplification curves.

In example 5, the examples 1, 2, 3, or any of the preceding examples are provided, wherein the adjusting the view is zooming out from the plurality of amplification curves.

In example 6, the examples 1, 2, 3, or any of the preceding examples are provided, wherein a first portion of the list is viewable on the display screen.

In example 7, the examples 1, 2, 3, or any of the preceding examples are provided, wherein a second portion of the list is viewable after scrolling the list down.

In example 8, the examples 1, 2, 3, or any of the preceding examples are provided, further comprising providing information about the sample in a reaction site after a user selects an indication of a reaction site from the list.

In example 4, the examples 1, 2, 3, or any of the preceding examples are provided, wherein the display screen is a touch screen.

In example 5, a method for identifying a reaction site associated with an amplification curve from a plurality of amplification curves is provided comprising: receiving amplification data from a plurality of reaction sites, wherein each reaction site contains a sample; generating a plurality of amplification curves from the amplification data; displaying a first portion of the plurality of amplification curves on a display screen; displaying a list of indications of reaction sites associated with the first portion of amplification curves alongside the first portion of amplification curves on the display screen; adjusting the view to display a second portion of the plurality of amplification curves; dynamically adjusting the list to display indications of reaction sites associated with the second portion of amplification curves alongside the second portion of amplification curves on the display screen, wherein the list is configured to be scrollable.

In example 6, the example 5 is provided, wherein the adjusting the view is zooming in on the plurality of amplification curves.

In example 7, the example 5 is provided, wherein the adjusting the view is zooming out from the plurality of amplification curves.

In example 8, the example 5 is provided, wherein a first portion of the list is viewable on the display screen.

In example 9, the example 5 and 8 are provided, wherein a second portion of the list is viewable after scrolling the list down.

In example 10, the example 5 is provided, further comprising: providing information about the sample in a reaction site after a user selects an indication of a reaction site from the list.

In example 11, the example 5 is provided, where the display screen is a touch screen.

In example 12, a computer-readable storage medium encoded with processor-executable instructions, the instruction for identifying a reaction site associated with an amplification curve from a plurality of amplification curves, is provided. The instructions comprising instructions for: receiving amplification data from a plurality of reaction sites, wherein each reaction site contains a sample; generating a plurality of amplification curves from the amplification data; displaying a first portion of the plurality of amplification curves on a display screen; displaying a list of indications of reaction sites associated with the first portion of amplification curves alongside the first portion of amplification curves on the display screen; adjusting the view to display a second portion of the plurality of amplification curves; dynamically adjusting the list to display indications of reaction sites associated with the second portion of amplification curves alongside the second portion of amplification curves on the display screen, wherein the list is configured to be scrollable.

In example 13, the example 12 is provided, wherein the adjusting the view is zooming in on the plurality of amplification curves.

In example 14, the example 12 is provided, wherein the adjusting the view is zooming out from the plurality of amplification curves.

In example 15, the example 12 is provided, wherein a first portion of the list is viewable on the display screen.

In example 16, the example 15 is provided, wherein a second portion of the list is viewable after scrolling the list down.

In example 17, the example 12 is provided, further comprising instructions for: providing information about the sample in a reaction site after a user selects an indication of a reaction site from the list.

In example 18, the example 12 is provided, where the display screen is a touch screen.

In example 19, a system for identifying a reaction site associated with an amplification curve from a plurality of amplification curves is provided, comprising: a processor; and a memory encoded instructions, executable by the processor, the instructions comprising instructions for: receiving amplification data from a plurality of reaction sites, wherein each reaction site contains a sample; generating a plurality of amplification curves from the amplification data; displaying a first portion of the plurality of amplification curves on a display screen; displaying a list of indications of reaction sites associated with the first portion of amplification curves alongside the first portion of amplification curves on the display screen; adjusting the view to display a second portion of the plurality of amplification curves; dynamically adjusting the list to display indications of reaction sites associated with the second portion of amplification curves alongside the second portion of amplification curves on the display screen, wherein the list is configured to be scrollable.

In example 20, the example 19 is provided, wherein the adjusting the view is zooming in on the plurality of amplification curves.

In example 21, the example 19 is provided, wherein the adjusting the view is zooming out from the plurality of amplification curves.

In example 22, the example 19 is provided, wherein a first portion of the list is viewable on the display screen.

In example 23, the example 22 is provided, wherein a second portion of the list is viewable after scrolling the list down.

In example 24, the example 19 is provided, further comprising instructions for: providing information about the sample in a reaction site after a user selects an indication of a reaction site from the list.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Although various embodiments have been described with respect to certain exemplary embodiments, examples, and applications, it will be apparent to those skilled in the art that various modifications and changes may be made without departing from the present teachings.

What is claimed is:

1. A method for identifying a reaction site associated with an amplification curve from a plurality of amplification curves, the method comprising:

receiving amplification data from a plurality of reaction sites, wherein each reaction site contains a sample;

generating a plurality of amplification curves from the amplification data;

displaying a first portion of the plurality of amplification curves on a display screen;

displaying a list of indications of reaction sites associated with the first portion of amplification curves alongside the first portion of amplification curves on the display screen;

shifting from a view of the first portion of the plurality of amplification curves to display a view comprising a second portion of the plurality of amplification curves, wherein at least a portion of the second portion of the plurality of amplification curves are not included within the first portion of the plurality of amplification curves; and dynamically adjusting the list to display indications of reaction sites associated with viewable amplification curves included in the second portion of the plurality of amplification curves alongside the second portion of the plurality of amplification curves on the display screen, wherein the list is configured to be scrollable.

2. The method of claim 1, further comprising adjusting a view of the first portion of the plurality of amplification curves or a view of the second portion of the plurality of amplification curves by zooming in.

3. The method of claim 1, further comprising adjusting a view of the first portion of the plurality of amplification curves or a view of the second portion of the plurality of amplification curves by zooming out.

4. The method of claim 1, wherein a first portion of the list is viewable on the display screen.

5. The method of claim 4, wherein a second portion of the list is viewable after scrolling the list down.

6. The method of claim 1, further comprising:

providing information about the sample in a reaction site after a user selects an indication of the reaction site from the list.

7. The method of claim 1, where the display screen is a touch screen.

8. A non-transitory computer-readable storage medium encoded with processor-executable instructions, the instruction for identifying a reaction site associated with an amplification curve from a plurality of amplification curves, the instructions comprising instructions for:

receiving amplification data from a plurality of reaction sites, wherein each reaction site contains a sample;

generating a plurality of amplification curves from the amplification data;

displaying a first portion of the plurality of amplification curves on a display screen;

displaying a list of indications of reaction sites associated with the first portion of amplification curves alongside the first portion of amplification curves on the display screen;

shifting from a view of the first portion of the plurality of amplification curves to display a view comprising a second portion of the plurality of amplification curves, wherein at least a portion of the second portion of the plurality of amplification curves are not included within the first portion of the plurality of amplification curves; and dynamically adjusting the list to display indications of reaction sites associated with viewable amplification curves included in the second portion of the plurality of amplification curves alongside the second portion of the plurality of amplification curves on the display screen, wherein the list is configured to be scrollable.

9. The computer-readable storage medium of claim 8, further comprising adjusting a view of the first portion of the plurality of amplification curves or a view of the second portion of the plurality of amplification curves by zooming in.

10. The computer-readable storage medium of claim 8, further comprising adjusting a view of the first portion of the plurality of amplification curves or a view of the second portion of the plurality of amplification curves by zooming out.

11. The computer-readable storage medium of claim 8, wherein a first portion of the list is viewable on the display screen.

12. The computer-readable storage medium of claim 11, wherein a second portion of the list is viewable after scrolling the list down.

13. The computer-readable storage medium of claim 8, further comprising instructions for:

providing information about the sample in a reaction site after a user selects an indication of the reaction site from the list.

14. The computer-readable storage medium of claim 8, where the display screen is a touch screen.

15. A system for identifying a reaction site associated with an amplification curve from a plurality of amplification curves, the system comprising:

a processor; and a memory encoded with instructions, executable by the processor, the instructions comprising instructions for:

receiving amplification data from a plurality of reaction sites, wherein each reaction site contains a sample;

generating a plurality of amplification curves from the amplification data;

displaying a first portion of the plurality of amplification curves on a display screen;

displaying a list of indications of reaction sites associated with the first portion of amplification curves alongside the first portion of amplification curves on the display screen;

shifting from a view of the first portion of the plurality of amplification curves to display a view comprising a second portion of the plurality of amplification curves, wherein at least a portion of the second portion of the plurality of amplification curves are not included within the first portion of the plurality of amplification curves; and dynamically adjusting the list to display indications of reaction sites associated with viewable amplification curves included in the second portion of the plurality of amplification curves alongside the second portion of the plurality of amplification curves on the display screen, wherein the list is configured to be scrollable.

16. The system of claim 15, further comprising adjusting a view of the first portion of the plurality of amplification curves or a view of the second portion of the plurality of amplification curves by zooming in.

17. The system of claim 15, further comprising adjusting a view of the first portion of the plurality of amplification curves or a view of the second portion of the plurality of amplification curves by zooming out.

18. The system of claim 15, wherein a first portion of the list is viewable on the display screen.

19. The system of claim 18, wherein a second portion of the list is viewable after scrolling the list down.

20. The system of claim 15, further comprising instructions for:

providing information about the sample in a reaction site after a user selects an indication of the reaction site from the list.

* * * * *